US012773338B2

(12) United States Patent
McCoy

(10) Patent No.: US 12,773,338 B2
(45) Date of Patent: Oct. 27, 2026

(54) SCOLIOSIS BRACE WITH INFLATABLE PRESSURE BLADDERS AND SCOLIOSIS TREATMENT METHODS USING THE SAME

(71) Applicant: D. Barry McCoy, Coventry, RI (US)

(72) Inventor: D. Barry McCoy, Coventry, RI (US)

( * ) Notice: Subject to any disclaimer, the term of this patent is extended or adjusted under 35 U.S.C. 154(b) by 370 days.

(21) Appl. No.: 18/498,095

(22) Filed: Oct. 31, 2023

(65) Prior Publication Data

US 2024/0139017 A1 May 2, 2024

Related U.S. Application Data

(60) Provisional application No. 63/381,985, filed on Nov. 2, 2022.

(51) Int. Cl.
*A61F 5/02* (2006.01)
*A61F 5/058* (2006.01)
*G16H 40/63* (2018.01)

(52) U.S. Cl.
CPC .............. *A61F 5/024* (2013.01); *A61F 5/022* (2013.01); *A61F 5/028* (2013.01); *A61F 5/05816* (2013.01); *G16H 40/63* (2018.01)

(58) Field of Classification Search
CPC .. A61F 5/012; A61F 5/02; A61F 5/022; A61F 5/024; A61F 5/026; A61F 5/028; A61F 5/05816
See application file for complete search history.

(56) References Cited

U.S. PATENT DOCUMENTS

| | | | |
|---|---|---|---|
| 5,360,392 | A | 11/1994 | McCoy |
| 5,632,723 | A | 5/1997 | Grim |
| 6,515,593 | B1 | 2/2003 | Stark et al. |
| 6,540,707 | B1 | 4/2003 | Stark et al. |
| 8,021,283 | B2 | 9/2011 | Sato et al. |
| 8,328,693 | B2 | 12/2012 | Sato |
| 9,545,536 | B2 | 1/2017 | Sato |
| 10,052,223 | B2 | 8/2018 | Turner |

(Continued)

FOREIGN PATENT DOCUMENTS

| | | | |
|---|---|---|---|
| CN | 101972182 | A | 2/2011 |
| CN | 105877886 | A | 8/2016 |

(Continued)

OTHER PUBLICATIONS

Lou, E., Chan, C., Raso, V., Hill, D., Moreau, M., Mahood, J., & Donauer, A. (2005). A smart orthosis for the treatment of scoliosis. Conference proceedings : . . . Annual International Conference of the IEEE Engineering in Medicine and Biology Society. IEEE Engineering in Medicine and Biology Society. Annual Conference, 2006, 1008-1011.

(Continued)

*Primary Examiner* — Keri J Nelson

(74) *Attorney, Agent, or Firm* — Hinckley Allen & Snyder; Stephen Holmes

(57) ABSTRACT

According to embodiments of the invention, a novel scoliosis brace includes inflatable pressure bladders which are cyclically controlled and monitored to increase and decrease pressure over a given treatment period. A treatment protocol monitors and tracks the quality and quantity of brace "wear time" to provide better data for modifying and/or increasing bladder pressures and cycle times over a long-term bracing period.

12 Claims, 4 Drawing Sheets

(56) References Cited

U.S. PATENT DOCUMENTS

| | | | | |
|---|---|---|---|---|
| 2009/0054818 | A1 | 2/2009 | Kaufman et al. | |
| 2009/0275871 | A1 | 11/2009 | Liu | |
| 2011/0230806 | A1 | 9/2011 | Lou et al. | |
| 2014/0221890 | A1* | 8/2014 | Thibeault | A61F 5/02<br>602/19 |

FOREIGN PATENT DOCUMENTS

| | | | |
|---|---|---|---|
| CN | 107411864 | A | 12/2017 |
| EP | 2664306 | B1 | 12/2014 |

OTHER PUBLICATIONS

Chalmers, E., Lou, E., Hill, D., Zhao, V. H., & Wong, M. S. (2012). Development of a pressure control system for brace treatment of scoliosis. IEEE transactions on neural systems and rehabilitation engineering : a publication of the IEEE Engineering in Medicine and Biology Society, 20(4), 557-563. https://doi.org/10.1109/TNSRE.2012.2192483.

Bansode, S., Shinde, T., Nimmagadda, M., Garapati, S., & Abdel-Qader, I. (2017). Design and implementation of regulated-pressure brace with on-board control and monitoring abilities for the treatment of scoliosis. 2017 Second International Conference on Electrical, Computer and Communication Technologies (ICECCT), 1-5.

Antonelli, M.G., Zobel, P.B., Raimondi, P., Raparelli, T., & Costanzo, G.D. (2010). An Innovative Brace With Pneumatic Thrusts For Scoliosis Treatment. International Journal of Design & Nature and Ecodynamics, 5, 354-367.

Lou, E., Venkateswaran, S., Hill, D.L., Raso, J.V., and Donauer, A., “An intelligent active brace system for the treatment of scoliosis,” in IEEE Transactions on Instrumentation and Measurement, vol. 53, No. 4, pp. 1146-1151, Aug. 2004, doi: 10.1109/TIM.2004.831458.

* cited by examiner

Default Brace Settings

| Level | Time On (minutes) | Time Off (minutes) | Pressure |
|---|---|---|---|
| 1 | 1 | 1 | 30 |
| 2 | 2 | 1 | 60 |
| 3 | 3 | 1 | 90 |
| 4 | 4 | 1 | 120 |

Save Default Brace Settings

SCOLIOSIS BRACE WITH INFLATABLE PRESSURE BLADDERS AND SCOLIOSIS TREATMENT METHODS USING THE SAME

CROSS-REFERENCE TO RELATED APPLICATIONS

This application claims the benefit of U.S. Provisional Patent Application No. 63/381,985, filed Nov. 2, 2022, the entire contents of which is incorporated herein by reference.

BACKGROUND OF THE DISCLOSURE (1) Field of the Invention: The instant invention generally relates to scoliosis bracing and treatment protocols, and more specifically to a novel scoliosis brace having inflatable pressure bladders which are cyclically controlled to increase and decrease pressure over a given treatment period and a treatment protocol which monitors and tracks the quality and quantity of brace "wear time" to modify and/or increase bladder pressures and cycle times over a long-term bracing period.

(2) Description of Related Art: Idiopathic scoliosis ("IS") is a curvature of the spine which may include vertebral rotation, affecting the rib cage and presenting deformities of the trunk. Treatment modalities for scoliosis are based on patient's physiologic maturity, curve severity, curve location, surface deformities, and the risk of progression.

Bracing is a common non-surgical method to control curve progression during the high-risk growth phase of adolescent patients. A brace typically comprises a hard plastic shell with internal localized pressure pads to provide passive mechanical support to the spine. A properly fitted brace (if used consistently) progressively applies corrective lateral pressure to targeted areas of the spinal column and in theory should reduce the curve with the goal of treatment being generally accepted to prevent further curve progression without surgical intervention.

To be effective, the brace must be worn consistently as prescribed and until the child has completed growth. However, many recent studies have questioned the effectiveness of bracing and therefore the efficacy of bracing still remains a controversial topic among pediatric orthopedic surgeons.

The most important determinant of the effectiveness of bracing management is compliance, both in terms of "quantity" (i.e. wearing the brace for the prescribed amount of time per day) and "quality" (i.e. while being worn the brace is providing the intended curve correction). To monitor compliance, the most common method is an honor system where the patient/family reports wear time. Other electronic monitoring methods, such as temperature sensors, and pressure switches and force sensors have been used to study compliance but these methods have significant practical limitations and none measured both the quantity and quality of brace usage at the same time. Even if wear time "quantity" is accurately reported and tracked over time, the "quality" of the wear time has been difficult to validate. Without known pressure values, meaningful conclusions about the effectiveness of bracing for any particular patient are difficult to draw.

SUMMARY OF THE DISCLOSURE

According to some embodiments of the invention, a novel scoliosis brace may include one or more inflatable pressure bladders in the thoracic and/or lumbar area(s) which are cyclically controlled and monitored to increase and decrease pressure over a given treatment period. A treatment protocol monitors and tracks the quality and quantity of brace "wear time" to provide better data for modifying and/or increasing bladder pressures and cycle times over a long-term bracing period.

Generally, the system comprises a novel scoliosis brace with an integrated inflatable bladder system, and external control device (cell phone/tablet) running a proprietary control and monitoring application, and may further include a back-end server which stores patient data, operating values and long term recorded wear data.

While embodiments of the invention have been described as having the features recited, it is understood that various combinations of such features are also encompassed by particular embodiments of the invention and that the scope of the invention is limited by the claims and not the description.

BRIEF DESCRIPTION OF THE DRAWING FIGURES

While the specification concludes with claims particularly pointing out and distinctly claiming particular embodiments of the instant invention, various embodiments of the invention can be more readily understood and appreciated from the following descriptions of various embodiments of the invention when read in conjunction with the accompanying drawings in which:

DETAILED DESCRIPTION OF THE EXEMPLARY EMBODIMENTS

Certain exemplary embodiments will now be described to provide an overall understanding of the principles of the structure, function, manufacture, and use of the device and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Further, to the extent that directional terms like top, bottom, up, or down are used, they are not intended to limit the systems, devices, and methods disclosed herein. A person skilled in the art will recognize that these terms are merely relative to the system and device being discussed and are not universal.

According to some embodiments of the invention, a novel scoliosis brace 10 includes inflatable pressure bladders which are cyclically controlled and monitored to increase and decrease pressure over a given treatment period. A treatment protocol program monitors and tracks the quality and quantity of brace "wear time" to provide better data for modifying and/or increasing bladder pressures and cycle times over a long-term bracing period.

More specifically, the overall system comprises a novel scoliosis brace 10 with an integrated inflatable bladder system 12, and external control device (cell phone/tablet) 14 running a proprietary control and monitoring application. Some embodiments of the system may further include a remote back-end server 16 which receives and stores patient data, operating values and long term recorded wear data for remote access by supervising physicians 18.

Figure 1:
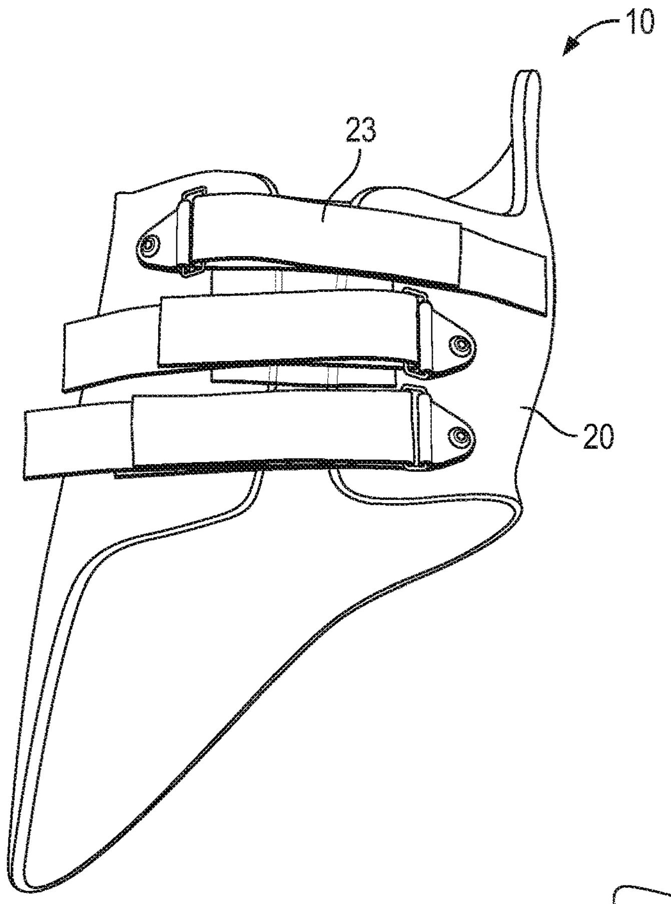
FIG. 1 is a front view of an exemplary embodiment of a scoliosis bracing system in accordance with the teachings of the present disclosure.
Figure 2:
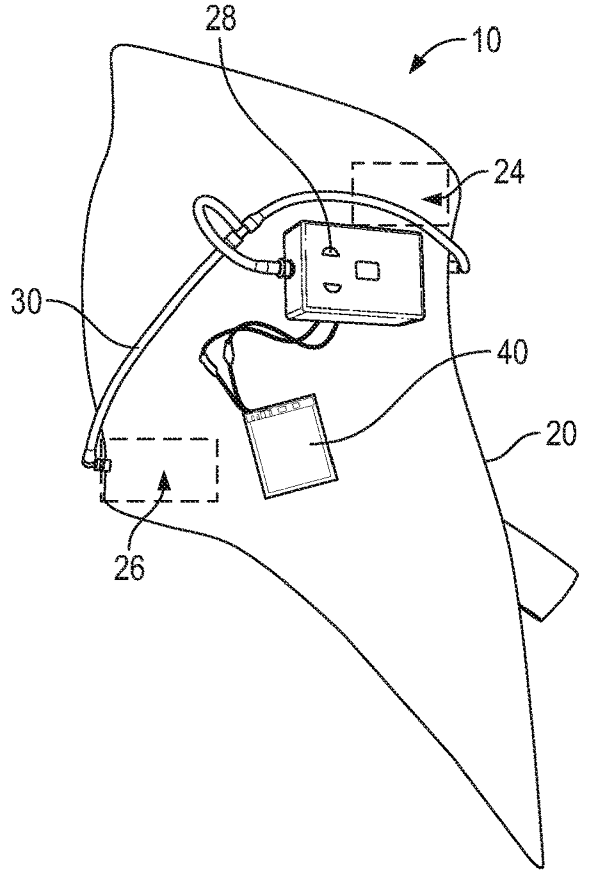
FIG. 2 is a rear view thereof showing the bladder inflation pump and control.
Figure 3:
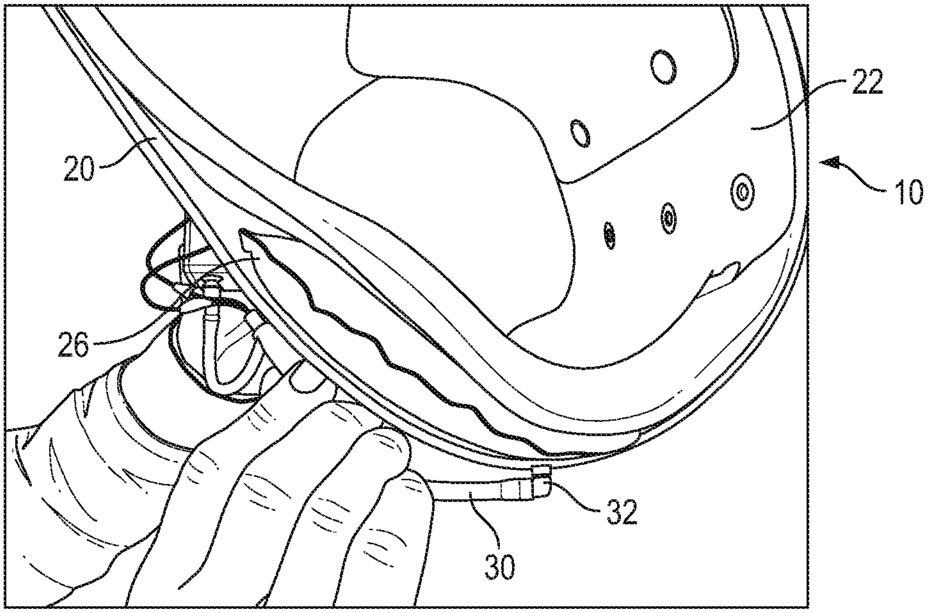
FIG. 3 is a bottom view thereof shower the lumbar bladder positioned between the padding and the outer shell.

An exemplary embodiment of a scoliosis brace 10 in accordance with the teachings of the invention is illustrated in FIGS. 1-3. The scoliosis brace 10 may comprise a rigid outer shell 20, an interior padding layer 22 disposed on an inner surface of the outer shell 20 and adjustable closure straps 23. The outer shell 20 may be custom form fit and molded to the individual user to provide proper external bracing support for the interior padding and bladder components.

One or more inflatable air bladders 24, 26 of predetermined shape and size are located between the outer shell 20 and the inner foam padding 22. Placement of the bladder(s) 24, 26 between the outer shell 20 and the inner foam padding 22 distributes bladder pressure more evenly over a broader surface area and prevents uncomfortable localized pressure points which are a common cause of non-compliant wear. The shape, size and position of the inflatable bladder(s) 24, 26 within the shell 20 are configured so as to be effective for applying more evenly distributed pressure to a targeted location(s) on the spine of a patient.

In some embodiments, the bladder(s) 24, 26 may be placed into a pocket formed between two foam layers.

As noted above, the air bladders 24, 26 may be shaped corresponding to the relative location of the respective bladder within the brace. For example, an upper thoracic bladder 24 may be generally shaped as a parallelogram while a lumbar bladder 26 may be generally shaped as a triangle or tear drop with the apex pointed towards the small of the back. Various progressively sized bladders may be provided so as to be interchangeable within the system to provide adaptability to various body size and to grow with adolescent patients.

The bladder system 12 further includes an air pump 28 in fluid communication with the inflatable bladder(s) 24, 26. Movement of air from the pump 28 to the bladders 24, 26 is accomplished with supply tubes 30 which are appropriately routed to the bladder(s) 24, 26. A single pump 28 may be provided to inflate two distinct bladders 24, 26.

To provide interchangeability of the bladders 24, 26, the supply tube termination ends and the bladder inlet ports 32 may be provided with releasable interfitting connections (see FIGS. 2 and 3).

Figure 4:
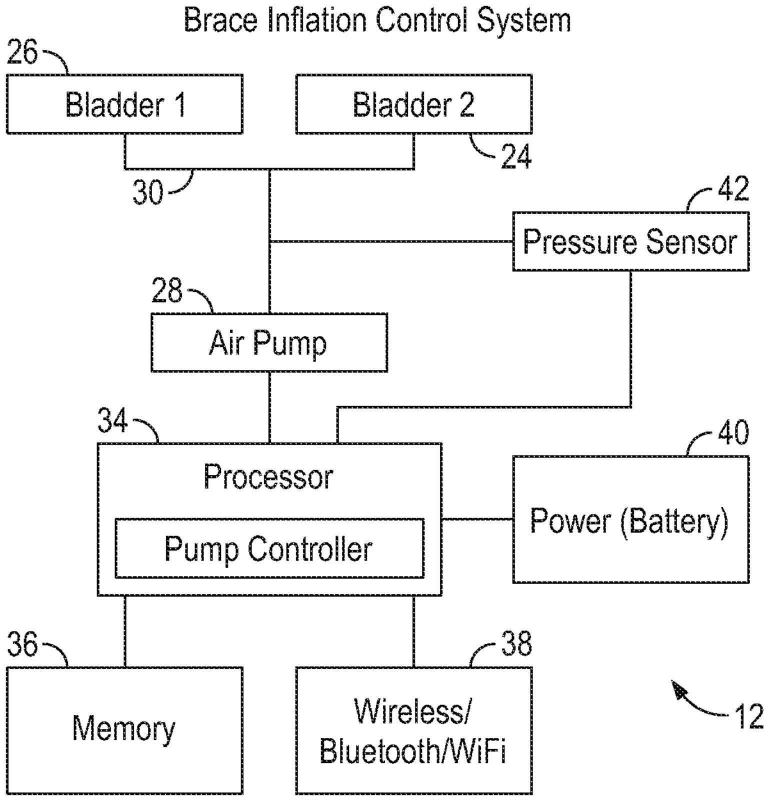
FIG. 4 is a schematic block diagram of the bladder inflation and control system.

An exemplary device level block diagram of the bracing system electronic and control components is illustrated in FIG. 4. A microcontroller/processor 34 in communication with the air pump 28 is operable for selectively controlling the air pump 28 to inflate and deflate the bladder(s) 24, 26 according to various operating values and protocols to be described hereinafter. The processor 34 may include associated memory 36 and a wireless communication transceiver 38, such as Bluetooth or WiFi. The inflation system 12 may further include a rechargeable power source (battery) 40. A pressure sensor 42 receives input from the air supply tubes 30 and communicates real time pressure data to the processor 34 for monitoring, analytics and long term data acquisition and aggregation.

The system may further include an external control device 14, such as a mobile phone or tablet, which is in wireless paired communication with the inflatable bladder system 12. Wireless communication may be accomplished by any known wireless transceiver 50 but may preferably comprise a Bluetooth paired connection or a direct WiFi connection with the bladder inflation system 12.

Figure 5:
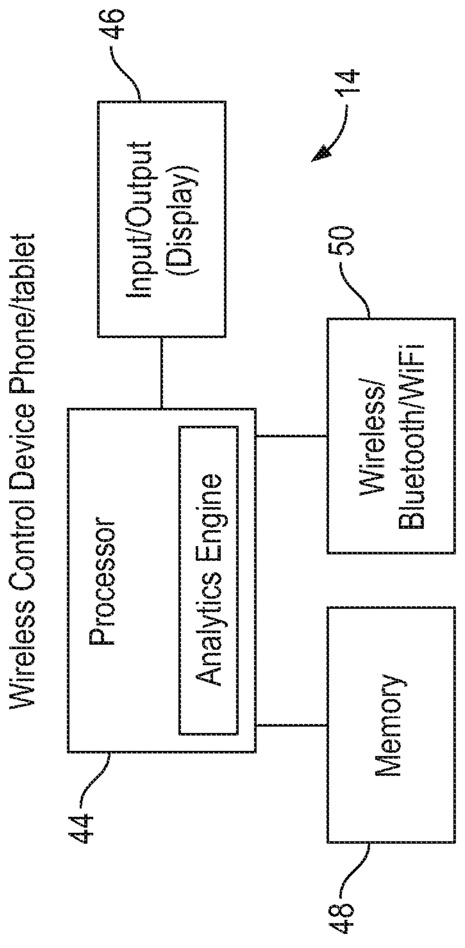
FIG. 5 is a schematic block diagram of the associated wireless control device.

A block diagram of an exemplary control device 14 is illustrated in FIG. 5. An exemplary external control device (cell phone/tablet) 12 may comprise an input/output user interface 46 (LCD touch screen display) for receiving input from the user and displaying output, a memory 48 which may include a table of stored operating values and a processor 44 coupled to the memory 48 and the user interface 46, and which is programmed with executable instructions including an analytics engine.

Figure 6:
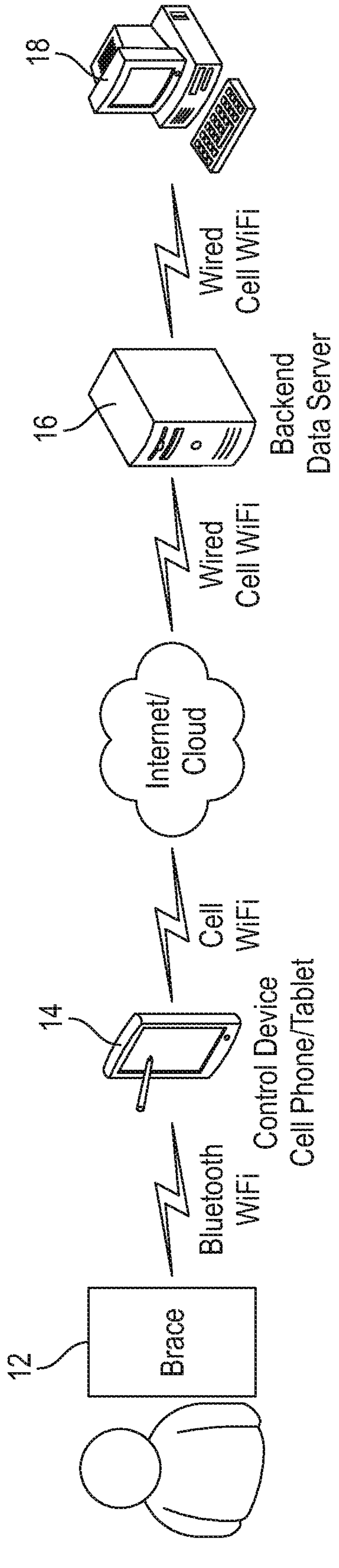
FIG. 6 is a schematic block diagram of the overall communication system including a remote server.

Referring to FIG. 6, the system 12 may also be controlled remotely by accessing the data server 16 directly and directing input to a specified device registered within the remote database/server system. The remote server 16 is also utilized for maintaining patient/user accounts and remotely storing aggregated user wear data for review and analysis by physicians overseeing treatment of the patient.

Figures 7, 8:
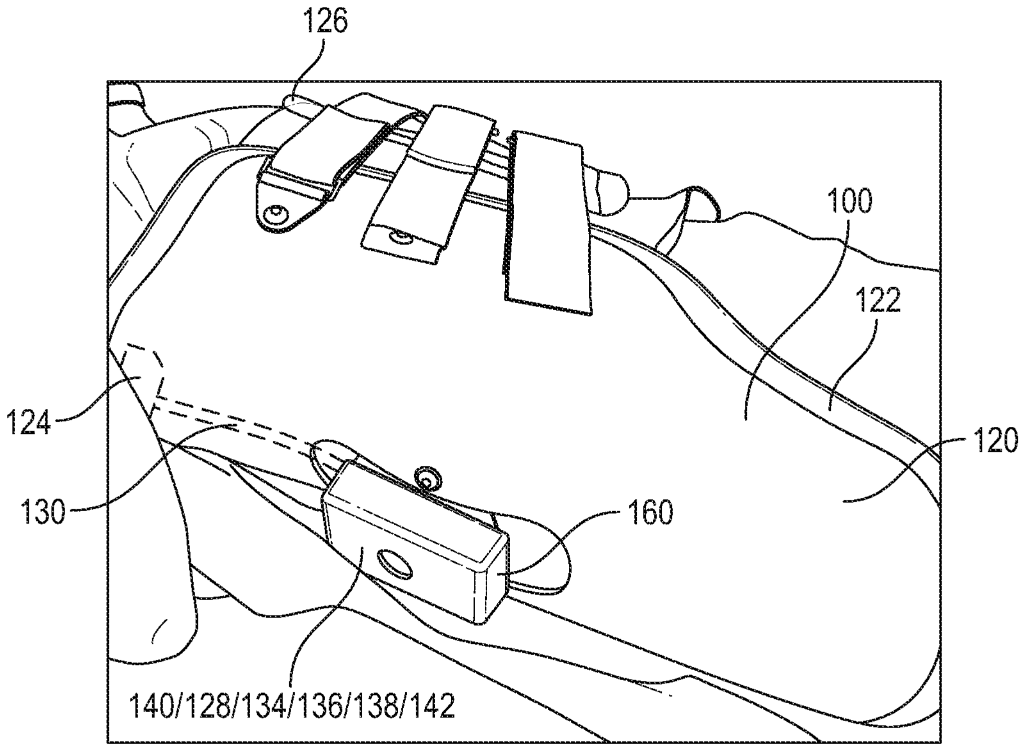
FIG. 7 is an exemplary table showing one example of progressive cycle times and pressures.
FIG. 8 is a perspective view of another exemplary embodiment with the air supply tubes positioned between the outer shell and the foam padding.

The stored operating values within the control memory 48 may include on and off cycles, on and off cycle times and progressive cycle pressures. An exemplary table of cycle times and pressure is shown in FIG. 7. The exemplary table is not intended to be limiting and may be fully customizable to individual patient needs and treatment protocols.

With respect to the operating values as noted, a critical premise of the present invention is a realization that timed cyclic pressure is more tolerable to the wearer and thus will promote more consistent and longer-term quality use, leading to improved outcomes. The operating times and pressure values can be completely customized based on individual patient needs, body type, BMI, severity of curvature, age, etc.

Generally, the methodology of the analytics system operating on the brace bladder and control device is as follows:

a) receiving input from a user to identify an operating value and to start and stop a timed wear cycle;
b) selectively controlling the air pump to cyclically inflate and deflate the bladder according to the operating value/predetermined pressure during the timed wear cycle;
c) operating a feedback loop which continuously monitors pressure of the bladder, d) selectively controlling the air pump to maintain the predetermined pressure at a constant level based on the feedback loop;

e) continuously recording pressure values during the timed wear cycle;

f) determining an effective wear time based on changes in the recorded pressure values;

g) calculating a bracing score based on said effective wear time; and h) displaying the bracing score at the conclusion of the timed wear cycle.

Prior art systems have attempted various methods for recording "effective wear time" but as noted above, these methods and systems relied heavily on physical switches (force sensors) and/or an honor system. The present analytics system uses the recorded pressure values from the feedback loop as a means of determining whether the brace is actually being worn. Changes in pressure on the bladder(s) 24, 26 during normal operation and normal active sleep patterns are highly indicative of actual wear time.

The bracing score is based on a 100-point system and is calculated based on an 8-hour sleep/wear cycle with the patient receiving 12.5 points per hour of normal effective wear time. A full 8-hour wear cycle would generate a score of 100, while a 7-hour wear time would generate a score of 87.5, etc. The point system gives young adults a familiar scoring system which they can easily relate to for effectiveness.

In a treatment regimen, it would be foreseen that with the bracing scores and improved wear tracking, the patient could increase the operating "level" to the next step approximately every three months with actual patient visits, or more quickly based on higher compliance score, or more slowly based on lower compliance scores. The system thus provides the physician a concrete data set of quality and quantity wear time on which to base future treatment.

As noted above, the scoliosis bracing system 12 may further comprise a remote server 16 in wireless communication with the external control device 14. Such a remote server 16 may comprise, for example, a PC or laptop with a user interface for receiving input and displaying output, a memory including a database of patient data wherein the patent data includes prescribed operating values, recorded wear data and bracing scores, a processor coupled to the memory and the user interface, and programmed with executable instructions including an analytics engine which is operable for receiving input from a user to set operating values and to retrieve recorded wear data, and for displaying output from the database based on the input.

The backend server 16 may in turn be accessed remotely from another PC or computer device 18 to provide an effective cloud-based operating system.

Referring to FIG. 8 there is shown another exemplary embodiment of a scoliosis brace including bladders 124, 126 (shown in dotted line) wherein the battery 140, pump 128 and various electronics (processor 134/pressure sensor 142/memory 136/wireless transceiver 138) are packaged within a common housing 160 mounted on the exterior of the shell 120 and the air supply tubes 130 are routed from the pump 128 into the brace shell 120 within the space between the shell 120 and the foam padding 122.

An exemplary scoliosis treatment method according to the invention may comprise the follow steps:

providing a scoliosis brace comprising,
- an outer shell; and
- a padding layer disposed on an inner surface of the outer shell, providing an inflatable bladder system comprising:
- at least one inflatable bladder of predetermined shape and size disposed in a predetermined position between the padding layer and the outer shell,
- the shape, size and position of the inflatable bladder being effective for applying pressure to a targeted location on the spine of a patient;
- an air pump in fluid communication with the inflatable bladder; and
- a controller in communication with the air pump operable for selectively controlling the air pump to inflate and deflate the bladder;

providing an external control device in wireless communication with the inflatable bladder system, the external control device comprising;
- a user interface for receiving input and displaying output;
- a memory including a table of operating values, wherein the operating values include on and off cycles, on and off cycle times and cycle pressures; and
- a processor coupled to the memory and the user interface, and programmed with executable instructions;

starting a timed wear cycle and an operating value;

selectively controlling the air pump to cyclically inflate and deflate the bladder according to the operating value during the timed wear cycle;

monitoring a feedback loop which continuously monitors pressure of the bladder, selectively controlling the air pump to maintain said predetermined pressure at a constant level based on said feedback loop;

continuously recording pressure values during the timed wear cycle;

stopping the timed wear cycle;

determining an effective wear time based on changes in said recorded pressure values;

calculating a bracing score based on said effective wear time; and displaying the bracing score at the conclusion of a timed wear cycle.

An exemplary treatment method may further comprise steps including increasing the operating values at predetermined calendar/timed intervals and at least partially based on consistent repeated bracing scores over said calendar intervals.

Treatment incentives or motivations may include but are not limited to: 1) instant feedback via a daily brace score; 2) comparison to others in the study to stimulate competition between others with a similar problem (all patients are blinded to others in the study); and 3) longitudinal tracking to measure progress over time to encourage compliance over the course of brace wear.

While there is shown and described herein certain specific structures embodying various embodiments of the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A scoliosis bracing system comprising:

a scoliosis brace comprising, an outer shell; and a padding layer disposed on an inner surface of the outer shell, an inflatable bladder system comprising:

at least one inflatable bladder of predetermined shape and size disposed within the outer shell wherein the at least one inflatable bladder comprises a first inflatable bladder disposed in a thoracic region of the brace, and a second inflatable bladder disposed in a lumbar region of the brace, an air pump in fluid communication with the at least one inflatable bladder; and a pump controller in communication with the air pump operable for selectively controlling the air pump to inflate and deflate the at least one bladder; and an external control device in wireless communication with the inflatable bladder system, said external control device comprising;

a user interface for receiving input and displaying output;

a memory including a table of operating values, wherein said operating values include on and off cycles, on and off cycle times and cycle pressures;

a processor coupled to the memory and the user interface, and programmed with executable instructions including an analytics engine which is operable for a) receiving input from a user to start and stop a timed wear cycle and an operating value;

b) selectively controlling the air pump to cyclically inflate and deflate the bladder according to said operating value during said timed wear cycle;

c) operating a feedback loop which continuously monitors pressure of the bladder, d) selectively controlling the air pump to maintain said predetermined pressure at a constant level based on said feedback loop;

e) continuously recording pressure values during said timed wear cycle; and f) determining an effective wear time based on changes in said recorded pressure values.

2. The scoliosis bracing system of claim 1 further comprising a remote server in wireless communication with said external control device, said remote server comprising:

a user interface for receiving input and displaying output;

a memory including a database of patient data wherein said patent data includes prescribed operating values, recorded wear data and bracing scores;

a processor coupled to the memory and the user interface, and programmed with executable instructions including an analytics engine which is operable for a) receiving input from a user to set operating values and retrieve recorded wear data; and b) displaying output from said database based on said input.

3. The scoliosis bracing system of claim 2 wherein the analytics engine is further operable for g) calculating a bracing score based on said effective wear time; and h) displaying said bracing score at the conclusion of said timed wear cycle.

4. The scoliosis bracing system of claim 1 wherein the at least one inflatable bladder is disposed in a predetermined position between the padding layer and the outer shell, said shape, size and position of said at least one inflatable bladder being effective for applying pressure to a targeted location on the spine of a patient.

5. The scoliosis bracing system of claim 4 wherein the analytics engine is further operable for g) calculating a bracing score based on said effective wear time; and h) displaying said bracing score at the conclusion of said timed wear cycle.

6. The scoliosis bracing system of claim 1 wherein the first inflatable bladder is generally parallelogram in shape and the second inflatable bladder is generally tear drop in shape.

7. The scoliosis bracing system of claim 1 wherein the analytics engine is further operable for g) calculating a bracing score based on said effective wear time; and h) displaying said bracing score at the conclusion of said timed wear cycle.

8. A scoliosis treatment method comprising the steps of:

providing a scoliosis brace comprising, an outer shell; and a padding layer disposed on an inner surface of the outer shell, providing an inflatable bladder system comprising:

at least one inflatable bladder of predetermined shape and size disposed in a predetermined positioned within the outer shell, said shape, size and position of said at least one inflatable bladder being effective for applying pressure to a targeted location on the spine of a patient;

an air pump in fluid communication with the inflatable bladder; and a controller in communication with the air pump operable for selectively controlling the air pump to inflate and deflate the bladder;

providing an external control device in wireless communication with the inflatable bladder system, said external control device comprising;

a user interface for receiving input and displaying output;

a memory including a table of operating values, wherein said operating values include on and off cycles, on and off cycle times and cycle pressures; and a processor coupled to the memory and the user interface, and programmed with executable instructions;

selecting of an operating value;

starting a timed wear cycle;

selectively controlling the air pump to cyclically inflate and deflate the bladder according to said operating value during said timed wear cycle;

monitoring a feedback loop which continuously monitors pressure of the bladder, selectively controlling the air pump to maintain said predetermined pressure at a constant level based on said feedback loop;

continuously recording pressure values during said timed wear cycle;

stopping the timed wear cycle;

determining an effective wear time based on changes in said recorded pressure values; and calculating a bracing score based on said effective wear time.

9. The treatment method of claim 8 further comprising the step of displaying said bracing score at the conclusion of a timed wear cycle.

10. The treatment method of claim 9 wherein said operating values are increased at predetermined calendar intervals at least partially based on consistent repeated bracing scores over said calendar intervals.

11. The treatment method of claim 8 wherein said operating values are increased at predetermined calendar intervals at least partially based on consistent repeated bracing scores over said calendar intervals.

12. A scoliosis treatment method comprising the steps of:

providing a scoliosis brace comprising, an outer shell; and a padding layer disposed on an inner surface of the outer shell, providing an inflatable bladder system comprising:

at least one inflatable bladder of predetermined shape and size disposed in a predetermined positioned within the outer shell, said shape, size and position of said at least one inflatable bladder being effective for applying pressure to a targeted location on the spine of a patient;

an air pump in fluid communication with the inflatable bladder; and a controller in communication with the air pump operable for selectively controlling the air pump to inflate and deflate the bladder;

providing an external control device in wireless communication with the inflatable bladder system, said external control device comprising;

a user interface for receiving input and displaying output;

a memory including a table of operating values, wherein said operating values include on and off cycles, on and off cycle times and cycle pressures; and a processor coupled to the memory and the user interface, and programmed with executable instructions;

selecting of an operating value;

starting a timed wear cycle;

selectively controlling the air pump to cyclically inflate and deflate the bladder according to said operating value during said timed wear cycle;

monitoring a feedback loop which continuously monitors pressure of the bladder, selectively controlling the air pump to maintain said predetermined pressure at a constant level based on said feedback loop;

continuously recording pressure values during said timed wear cycle;

stopping the timed wear cycle;

determining an effective wear time based on changes in said recorded pressure values;

calculating a bracing score based on said effective wear time; and increasing operating values at predetermined calendar intervals at least partially based on consistent repeated bracing scores over said calendar intervals.

* * * * *